United States Patent [19]

Nomura et al.

[11] Patent Number: 5,163,932
[45] Date of Patent: Nov. 17, 1992

[54] DISPOSABLE WEARING ARTICLE OF PANTS TYPE

[75] Inventors: Hironori Nomura, Iyomishima; Takamitsu Igaue; Hiroyuki Tanji, both of Kawanoe; Hirofumi Ohnishi, Iyomishima; Tohru Sasaki, Kawanoe, all of Japan

[73] Assignee: Uni-Charm Corporation, Ehime, Japan

[21] Appl. No.: 781,581

[22] Filed: Oct. 23, 1991

[30] Foreign Application Priority Data

Oct. 25, 1990 [JP] Japan .......................... 2-111729[U]

[51] Int. Cl.5 .............................................. A61F 13/15
[52] U.S. Cl. ................................ 604/385.2; 604/396; 2/401
[58] Field of Search .................. 604/358, 385.1, 385.2, 604/394, 396; 2/111, 400, 401, 402, 406

[56] References Cited

U.S. PATENT DOCUMENTS

| | | | |
|---|---|---|---|
| 2,581,904 | 1/1952 | Burns | 604/394 |
| 3,488,778 | 1/1970 | Goujon et al. | 604/358 X |
| 3,560,292 | 2/1971 | Butter | 2/406 X |
| 3,599,640 | 8/1971 | Larson | 2/406 X |
| 4,610,680 | 9/1986 | LaFleur | 604/385.2 |
| 4,205,679 | 6/1980 | Repke et al. | 604/385.2 X |
| 4,619,649 | 10/1986 | Roberts | 604/385.2 X |
| 4,743,241 | 5/1988 | Igaue et al. | 604/385.2 |
| 4,960,414 | 10/1990 | Meyer | 604/394 X |
| 5,080,741 | 1/1992 | Nomura et al. | 604/358 X |

FOREIGN PATENT DOCUMENTS

| | | |
|---|---|---|
| 0187727 | 7/1986 | European Pat. Off. . |
| 20274753 | 7/1988 | European Pat. Off. . |
| 0300615 | 1/1989 | European Pat. Off. ............ 604/358 |
| 0412549 | 2/1991 | European Pat. Off. . |
| 2001659 | 7/1971 | Fed. Rep. of Germany .......... 2/402 |
| 1189649 | 10/1959 | France ................................. 604/396 |
| 8907923 | 9/1989 | PCT Int'l Appl. .................. 604/396 |
| 2235125 | 2/1991 | United Kingdom . |
| 2245149 | 1/1992 | United Kingdom . |
| 88/07337 | 10/1988 | World Int. Prop. O. . |

Primary Examiner—David Isabella
Assistant Examiner—Mary Beth O. Jones
Attorney, Agent, or Firm—Fred Philpitt

[57] ABSTRACT

A disposable wearing article of pants type having a front body and a rear body comprising respectively at least a liquid-permeable topsheet and a liquid-impermeable backsheet, and elastic members along a waist-hole and respective leg-holes. The front and rear bodies are attached together along their laterally opposite side edges. The longitudinally opposite ends of the respective elastic members are located on the opposite side edges of the front and rear bodies, and the opposite side edges of the front and rear bodies are intermittently attached together so as to avoid the elastic members.

3 Claims, 3 Drawing Sheets

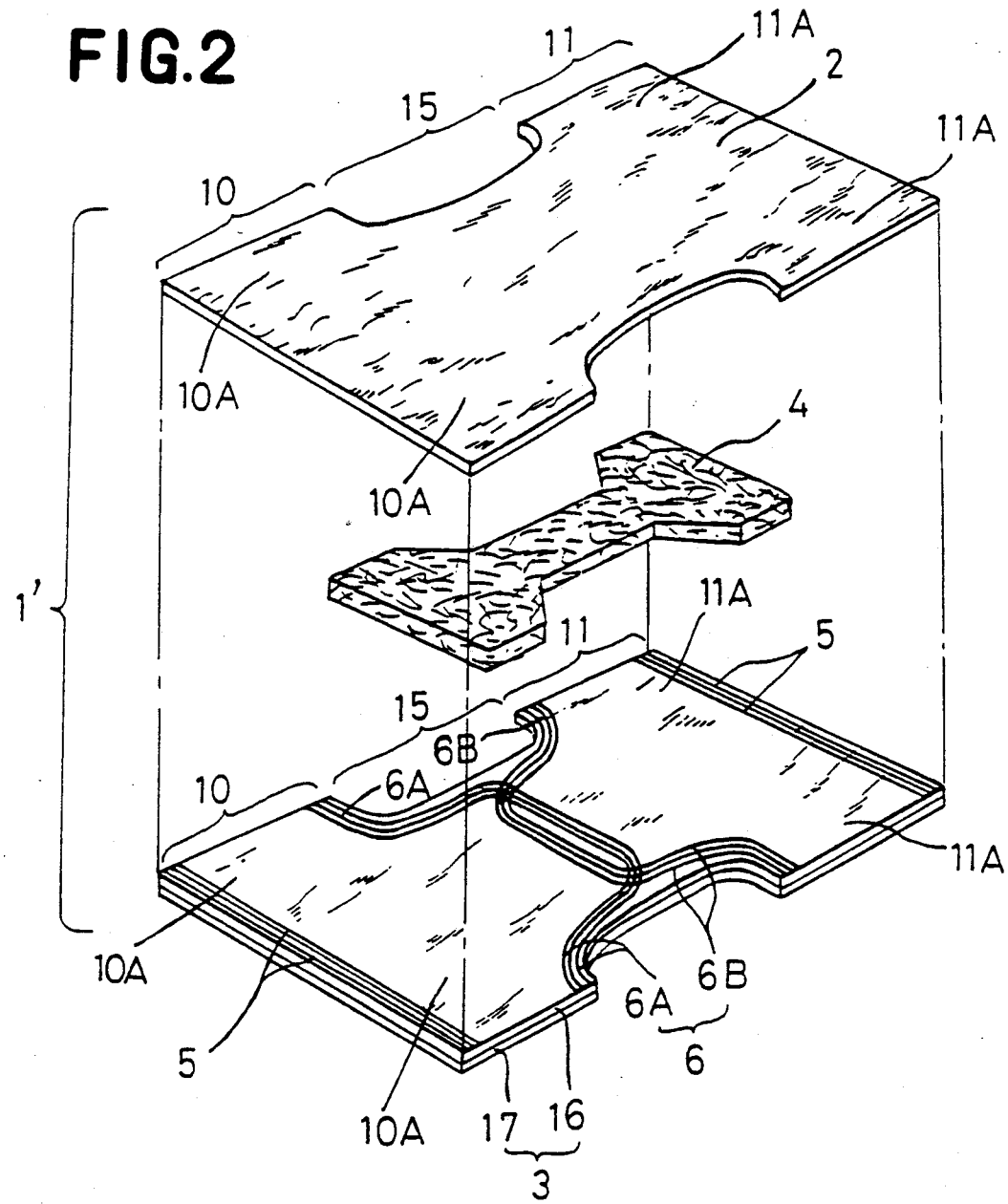

DISPOSABLE WEARING ARTICLE OF PANTS TYPE

BACKGROUND OF THE INVENTION

The present invention relates to a disposable wearing article of pants type and, more particularly, to such an article having laterally opposite side edges defined by bonding lines along which front and rear bodies are intermittently bonded together.

Disposable wearing articles such as training pants or a diaper basically comprises a liquid-permeable topsheet, a liquid-impermeable backsheet, and often, particularly in the case of a diaper, an absorbent core sandwiched between these top- and backsheets. In addition to these basic components, such a wearing article of the prior art usually includes elastic members provided in association with waist- and leg-holes, respectively, in order to provide a wearing fitness and a body fluids leakage preventing function. In regard to the types of such an article, on the other hand, besides the so-called open type which has been extensively used, the pants type has recently attracted consumers' attention because of its easiness for use. Specifically, the pants type is advantageous, for example, in that a good wearing fitness is obtained, the trouble of body fluids leakage possibly occurring around the waist- and/or leg-holes can be substantially prevented and the wearing procedure is very easy.

SUMMARY OF THE INVENTION

The present invention is directed to a disposable wearing article of pants type comprising at least a liquid-permeable topsheet, a liquid-impermeable backsheet and elastic members associated with a waist-hole and leg-holes, respectively, wherein laterally opposite side edges of said wearing article are formed by bonding lines along which front and rear bodies are bonded together. According to the well known techniques, said bonding has been achieved by bonding the front body and the rear body together along single or plural continuous bonding lines each extending from the waist-hole to the associated leg-hole. However, it has been found that such bonding lines necessarily obstruct a desired longitudinal stretchability of said wearing articles such as a disposable diaper of the pants type. Overcoming of such a problem is essential particularly when the diaper of the pants type is constructed from any stretchable materials to improve stretchability of this diaper. Additionally, said bonding lines often result in a structure of, for example, the pants type diaper being air-tight and makes it difficult to get good air-permeability that is required particularly for the pants type diaper. Moreover, the process of forming said bonding lines along said laterally opposite side edges containing therein said elastic members will be far more complicated than in the case of said laterally opposite side edges containing therein none of the elastic members.

Accordingly, it is a principal object of the present invention to provide a disposable wearing article of pants type having a novel bonding structure on said laterally opposite side edges and thereby to solve the various problems as have been mentioned above.

The object set forth above is achieved, in accordance with the present invention, by a disposable wearing article of pants type including a liquid-permeable topsheet and a liquid-impermeable backsheet wherein front and rear bodies are bonded together along laterally opposite side edges thereof and there are provided elastic members associated with a waist-hole and respective leg-holes, characterized by that said elastic members are sandwiched between said top- and backsheets, longitudinally opposite ends of the respective elastic members are located on said laterally opposite side edges of said front and rear bodies and said laterally opposite side edges of said front and rear bodies are intermittently bonded together so as to avoid said longitudinally opposite ends of the elastic members.

According to a preferred embodiment, said laterally opposite side edges are provided with grip-ears extending outwardly from said wearing article.

According to another preferred embodiment, both said liquid-permeable topsheet and said liquid-impermeable backsheet comprise elastically stretchable sheets.

According to still another preferred embodiment, each of said elastic members comprises a plurality of elements.

The disposable wearing article of pants type such as disposable diaper of pants type constructed according to the present invention has its laterally opposite side edges defined by the bonding lines along which the front body and the rear body are intermittently bonded together so that each of said laterally opposite side edges has alternately bonded zones and non-bonded zones. The non-bonded zones remains stretchable, contributing to improve a longitudinal stretchability of said pants type wearing article, on one hand, and laterally form openings serving to communicate the interior with the exterior of said pants type wearing article, allowing said pants type wearing article to obtain an improved air-permeability, or a breathing effect.

Furthermore, a special arrangement that said bonding is carried out so as to avoid the longitudinally opposite ends of the respective elastic members not only facilitates the work of bonding but also makes it unnecessary to employ a special procedure in order to arrange the elastic members so that the longitudinally opposite ends thereof may not locate on laterally opposite side edges of the front and rear bodies during said work of bonding.

Additionally, said wearing article of pants type once put on a wearer can be easily removed from the wearer by tearing away the front and rear bodies from each other along said bonding lines advantageously with a feel of moderate tearing resistance just as experienced when a zipper is opened. Such tearing off is further facilitated by providing the laterally opposite side edges of the article with the grip-ears.

With use of the liquid-permeable sheet as the topsheet and the liquid-impermeable sheet as the backsheet, respectively, said intermittent bonding never obstructs longitudinal stretchability of the wearing article and assures the wearing article to maintain a good air-permeability, or breathing effect.

Now the invention will be described in reference with embodiments illustrated by the accompanying drawings.

BRIEF DESCRIPTION OF THE DRAWINGS

FIG. 2 is an exploded perspective view of the diaper shown by FIG. 1;

PREFERRED EMBODIMENTS OF THE INVENTION

Embodiment 1

Figure 1:
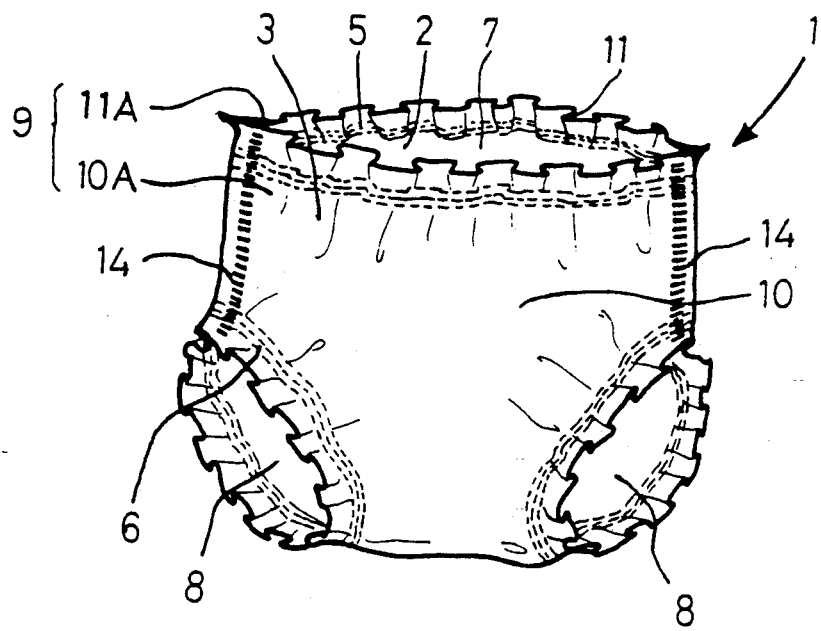
FIG. 1 is a perspective view showing diaper as a first embodiment of the invention.

Referring to FIG. 1 which is a perspective view showing a disposable diaper of pants type as a specific embodiment of the invention, the diaper 1 comprises a liquid-permeable topsheet 2, a liquid-impermeable backsheet 3, an absorbent core 4 (See FIG. 2), rubber threads 5, i.e. elastic members associated with a waist-hole 7 and rubber threads 6, i.e. elastic members associated with leg-holes 8. Respective circumferential edges of the waist-hole 7 and the leg-holes 8 form gathers under contraction of the associated rubber threads 5, 6. A front body 10 and a rear body 11 are welded together at the laterally opposite side edges 9, i.e., at their respective laterally opposite side edges 10A, 11A, to form the diaper 1 of pants type. It should be noted here that the diaper 1 is, in general, substantially symmetric in the lateral direction. It should be also understood that the absorbent core 4 incorporated into this specific embodiment is not necessarily essential to implement the present invention.

Referring to FIG. 2, the diaper 1 of FIG. 1 assembled on a continuous production line is illustrated in an exploded perspective view. Viewed in the longitudinal direction the diaper comprises the front body 10, the crotch zone 15 and the rear body 11 and, viewed in the direction of thickness, the diaper 1 comprises the topsheet 2, the absorbent core 4 and the backsheet 3. The topsheet 2 is made of elastically stretchable nonwoven fabric which is, in turn, prepared by entanglement treatment under water jet and successive heat-crimping of thermoplastic fibers, and the absorbent core 4 is preferably molded from fluffy pulp mixed with suitable water-absorptive polymer of 5 to 15% by weight. The backsheet 3 is made of two layers intermittently welded together with hot melt adhesive, one of said layers comprising an elastically stretchable liquid-impermeable sheet 16 of thermoplastic polyethylene elastomer and the other layer comprising stretchable nonwoven fabric 17 prepared by said entanglement treatment and successive heat-crimping of thermoplastic fibres. Said liquid-impermeable sheet 16 is opposed to the topsheet 2 with interposition of the absorbent core 4 and said nonwoven fabric 17 defines the outer surface of the diaper 1. Obviously, the liquid-impermeable sheet 16 serves to provide the backsheet 3 with liquid-impermeability and the nonwoven fabric 17 serves to provide the diaper's outer surface with soft touch. Intermittently bonding the liquid-impermeable sheet 16 and the nonwoven fabric 17 together allows the backsheet 3 to obtain an improved strength without a loss of its stretchability. The backsheet 3 has on the liquid-impermeable sheet 16 said rubber threads 5, i.e. the elastic members associated with the waist-hole and said rubber threads 6, i. e. the elastic members associated with the leg-holes, more specifically, rubber threads 6A, 6B associated with the respective leg-holes. Each of these elastic members can be comprised of a plurality of individual elastic threads, elastic elements and are intermittently bonded to said liquid-impermeable sheet 16 with hot melt adhesive under their stretched conditions. It should be noted that the partial lengths of the rubber threads 6A, 6B extending between a pair of their intersecting points in the crotch zone 15 are substantially non-stretched. The rubber threads 5, 6A, 6B, i.e. the elastic members may be of the materials as well as the configurations well known in the field of disposable diaper, for example, of thread-like or ribbon-like elastic members. These rubber threads 5, 6A, 6B are continuously fed along the flow direction on a continuous production line of the diaper 1, i.e., transversely of the diaper 1 so that their opposite cut off ends are brought onto the backsheet side edges corresponding to the laterally opposite side edges 9 (See FIG. 3). Layout of the rubber threads 6A, 6B on the liquid-impermeable sheet 16 are such that these rubber threads 6A, 6B are pairly laid out to provide the respective elastic members (rubber threads 6 in FIG. 1) for the respective substantially circular leg-holes 8. Details of such layout will not be further referred to.

The topsheet 2 and the backsheet 3 are identical to each other in their outer peripheries and have portions outside the absorbent core 4 so that these two sheets 2, 3 are intermittently welded together within said portions. A laminate 1' (See FIG. 2) thus obtained is folded in two along a longitudinally middle line with the topsheet 2 facing inward and the front body 10 being laid on the top of the rear body 11. Then said front and rear bodies 10, 11 are welded together by the welding lines 14 along respective laterally opposite side edges 10A, 11A thereof to form the diaper 1 of pants type. During this process of lamination, the rubber threads 5, 6A on the front body 10 are substantially opposed to the rubber threads 5, 6B on the rear body 11, respectively, to form the substantially continuous elastic members associated with the waist-hole 7 and the leg-holes 8, respectively.

Figure 3:
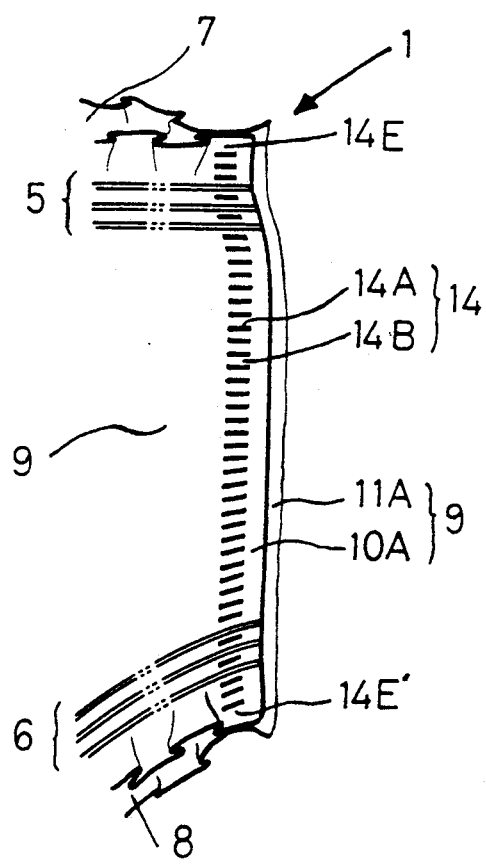
FIG. 3 is a fragmentary enlarged view of the diaper shown by FIG. 1.

Referring to FIG. 3, one of said laterally opposite side edges 9 inclusive of the welding line 14 is fragmentarily illustrated on an enlarged scale. Each of said laterally opposite side edges 9 comprises the side edges 10A, 11A of the front and rear bodies 10, 11, respectively. The welding line 14 comprises welded zones 14A in which the materials of the front and rear bodies 10, 11 are welded together by the ultrasonic welding technique and non-welded zones 14B in which said ultrasonic welding has not occurred, said welded zones 14A and said non-welded zones 14B alternating. The welding line 14 extends from the waist-hole 7 to the associated leg-hole 8. A major part of each welding line 14 is defined by alternating pattern such that the welded zones 14A of approximately 5×1mm (width by height) and the non-welded zones 14B of approximately 5×1.5mm (width by height) alternate. However, it will be apparent from FIG. 3 that, adjacent the elastic members for the respective leg-holes the welded zones 14A are slanted so as to extend substantially in parallel to the rubber threads 6A, 6B, respectively. The rubber threads 5, 6A, 6B are free from said ultrasonic welding carried out along the welding lines 14, i.e. they occupy said non-welded zones 14B. Upper end and/or lower end of each welding line 14 may be provided with non-welded zones 14E, 14E' being slightly larger than the remaining ones 14B so that the front and rear bodies can be easily torn away from each other along the welding line 14 by holding these non-welded zones 14E, 14E'. When each of the welded zones 14A is dimensioned so as to have a width of 0.5 to 20mm, preferably 1 to 15mm, as measured laterally of the diaper, a height of 0.5 to 30mm, preferably 1 to 15mm vertically of the diaper 1 and to occupy 40 to 90%, preferably 50 to 80% of a total area of the each welding line 14 extending from the waisthole 7 to the associated leg-hole 8, the welded zones 14A may have any configurations and repetition patterns so long as said elastic members are free from the ultrasonic welding. However, the welded zones 14A occupying less than 40% with respect to the total area of each welding line 14 might cause troubles such as a deficient strength of the welding line 14 and a leakage of body fluids. On the contrary, the ° welded zones 14A occupying 90% or more might significantly obstruct stretchability as well as air-permeability.

The diaper 1 obtained in the manner as has been described hereinabove is skillfully provided with a stretchability in the longitudinal direction of the diaper 1 owing to the presence of the non-welded zones 14B and thereby provided with a good fitness desired for the elastically stretchable diaper 1. In the non-welded zones 14B, there is established an air communication between the interior and the exterior of the diaper 1 and thereby a good air-permeable, on air breathing is obtained in spite of employing the liquid-impermeability sheet 16. In the process of ultrasonic welding, the zones of the laterally opposite side edges 9 in which the rubber threads 5, 6A, 6B having locally different thickness as well as hardness are present are free from said ultrasonic welding treatment, so the welding machine or equipment may be correspondingly designed, more specifically, designed so as to keep said zones from being welded and thereby the desired welding effect may be conveniently achieved.

For removal of the pants type diaper 1 from the wearer, the front body 10 and the rear body 11 may be held at the portions of their side edges 9 extending outside the welding line and pulled away from each other. In this way, the front and rear bodies 10, 11 can be easily torn away from each other. In addition, the repetitive pattern of the welded zones 14A and the non-welded zones 14B provides a feel of tear off resistance just like the feel experienced when a zipper is handled.

Figure 4:
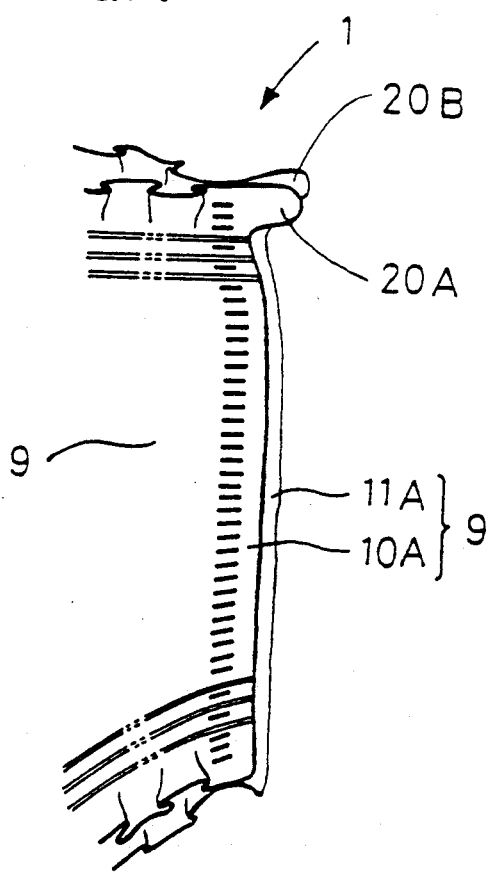
FIGS. 4 and 5 are fragmentary enlarged perspective views showing another embodiment of the invention.

Referring to FIG. 4, there is illustrated by way of example an arrangement that the front body 10 and the rear body 11 are provided at their side edges 10A, 11A with grip-ears 20A, 20B, respectively, extending outwardly from the respective side edges 10A, 11A. These ears 20A, 20B may be formed integrally with the topsheet 2 and/or the backsheet 3, or separately of these sheets 2, 3.

Embodiment 2

Figure 5:
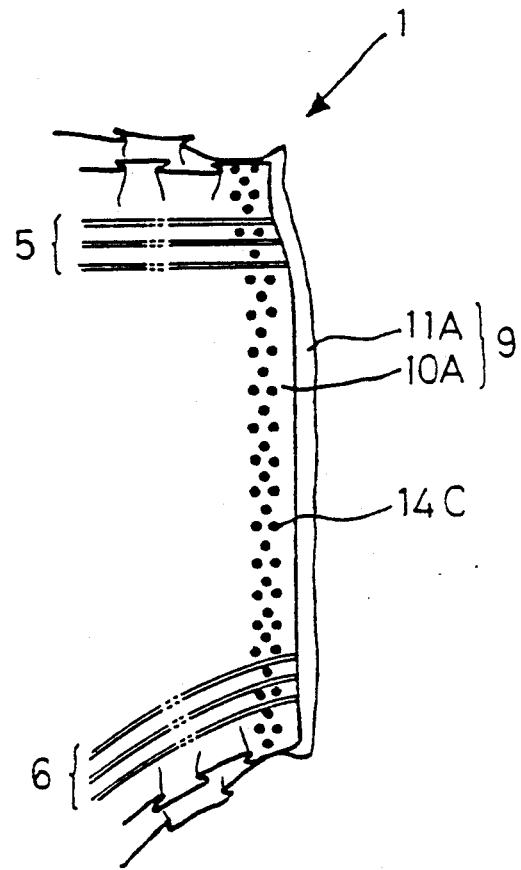

Referring to FIG. 5, there is illustrated Embodiment 2 of the invention which is basically similar to the diaper 1 as has previously been described as Embodiment 1 except that a bonding line 14 comprising of spots 14C has a lateral width of approximately 10mm, instead of ultrasonic-welding line 14, spots 14C of the hot melt adhesive each having a diameter of 2 to 4mm, and said adhesive spots occupy approximately 60% of the total area of the bonding line 14. Also in this embodiment, the adhesive spots 14C are applied so as to avoid the rubber threads 5, 6A, 6B.

The diaper 1 obtained according to this embodiment not only provides a desired stretchability owing to the presence of the non-bonded zones among the adhesive spots 14C but also a good air-permeability and other effects as obtained by Embodiment 1.

Embodiment 3

Figure 6:
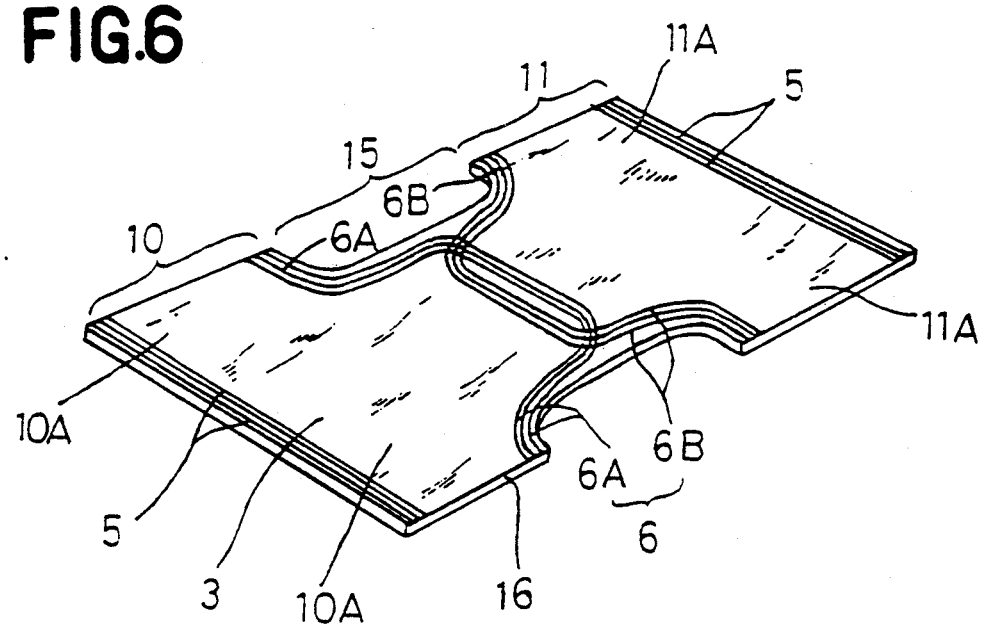
FIG. 6 is a perspective view showing a backsheet in further another embodiment of the invention.

FIG. 6 is a perspective view illustrating the backsheet 3 in embodiment 3 of the invention which is similar to the diaper 1 of Embodiment 1 except that said backsheet 3 has a modified arrangement. According to this embodiment, the topsheet 2 comprises, similarly to Embodiment 1, the elastically stretchable nonwoven fabric sheet made of heat crimped thermoplastic fibres intertwined, i. e. entangled under the treatment of high pressure water jet and the absorbent core 4 is also identical to that employed in Embodiment 1. However, the backsheet 3 comprises, as shown by FIG. 6, a monolayered elastically stretchable liquid-impermeable sheet 16 made of thermoplastic polyethylene elastomer. Such modified arrangement allows a manufacturing cost to be effectively reduced with respect to the previous embodiments.

What is claimed is:

1. A disposable wearing article of pants type that comprises
    (a) an absorbent core having a topside and a bottom side,
    (b) a topsheet on the topside of said absorbent core, and a backsheet on the bottom side of said absorbent core, said topsheet and backsheet not only covering the entire topside and bottom side of said absorbent core, but in addition extending laterally beyond the absorbent core to form two side sections,
    (c) said topsheet, backsheet and absorbent core being assembled together in folded over disposition to form two leg openings, a waist opening, a front body and a rear body, said side sections extending from the top of said leg openings to said waist opening and elongated elastic members associated with both said leg openings and said waist opening,
    (d) said two side sections each being joined together along the entire length of said side sections by sealing means consisting of a series of alternating spaced apart adhered areas and non-adhered area,
    (e) said elastic members being sandwiched between said topsheet and said backsheet, the longitudinal ends of said elongated elastic members being located on the edges of said side sections, and
    (f) said longitudinal ends of said elastic members being located in said non-adhered areas.

2. A wearing article as recited in claim 1, wherein said side sections are provided with grip-ears extending outwardly from the upper portions of said side sections.

3. A wearing article as recited in claim 1, wherein both said topsheet and said backsheet are elastically stretchable sheets.

* * * * *